United States Patent
Metayer et al.

(10) Patent No.: US 9,632,063 B2
(45) Date of Patent: Apr. 25, 2017

(54) NON-DESTRUCTIVE ULTRASOUND TESTING OF STRUCTURES MADE OF COMPOSITE MATERIAL

(71) Applicants: AIRBUS OPERATIONS (SAS), Toulouse (FR); EUROPEAN AERONAUTIC DEFENCE AND SPACE COMPANY EADS FRANCE, Paris (FR)

(72) Inventors: Patrick Metayer, Mauzac (FR); Marion Pages, Toulouse (FR)

(73) Assignees: Airbus Operations (SAS), Toulouse (FR); European Aeronautic Defence and Space Company Eads France, Paris (FR)

( * ) Notice: Subject to any disclaimer, the term of this patent is extended or adjusted under 35 U.S.C. 154(b) by 211 days.

(21) Appl. No.: 14/407,276

(22) PCT Filed: Jun. 17, 2013

(86) PCT No.: PCT/EP2013/062518
§ 371 (c)(1),
(2) Date: Dec. 11, 2014

(87) PCT Pub. No.: WO2013/189885
PCT Pub. Date: Dec. 27, 2013

(65) Prior Publication Data
US 2015/0160166 A1      Jun. 11, 2015

(30) Foreign Application Priority Data
Jun. 19, 2012   (FR) .................................... 12 55720

(51) Int. Cl.
*G01N 29/24*   (2006.01)
*G01N 29/44*   (2006.01)
*G01N 29/07*   (2006.01)

(52) U.S. Cl.
CPC ............. *G01N 29/07* (2013.01); *G01N 29/24* (2013.01); *G01N 29/44* (2013.01);
(Continued)

(58) Field of Classification Search
CPC ........ G01N 29/07; G01N 29/24; G01N 29/44; G01N 2291/011; G01N 2291/0231; G01N 2291/045; G01N 2291/106
(Continued)

(56) References Cited

U.S. PATENT DOCUMENTS 4,205,554 A * 6/1980 Uchida .............. G01N 29/0609
                                                        73/626
5,032,734 A * 7/1991 Orazio, Jr. ............. G01N 21/21
                                                        250/225
(Continued)

FOREIGN PATENT DOCUMENTS

| FR | 2 992 064 | 12/2013 |
| GB | 2 336 676 | 10/1999 |
| JP | 04-301762 | 10/1992 |

OTHER PUBLICATIONS

International Search Report for PCT/EP2013/062518, mailed Jul. 25, 2013, Couteau, Olivier, 2 pages.

*Primary Examiner* — J M Saint Surin
(74) *Attorney, Agent, or Firm* — Nixon & Vanderhye P.C.

(57) ABSTRACT

The invention relates to a diagnostic apparatus 1 for detecting delamination in the thickness of a panel of laminated composite. The diagnostic apparatus can be used to inspect a panel having a non-constant thickness along its length. The diagnostic apparatus comprises an ultrasonic probe 30 intended to be brought into contact with the front face of the panel to be inspected, an electronic device 40 for controlling the emission and reception of ultrasonic pulses 51 by the
(Continued)

ultrasonic probe 30, and a display device 41 having, notably, indicators showing the presence or absence of delamination in the panel.

9 Claims, 5 Drawing Sheets

(52) U.S. Cl.
 CPC ... *G01N 29/4427* (2013.01); *G01N 2291/011* (2013.01); *G01N 2291/0231* (2013.01); *G01N 2291/0289* (2013.01); *G01N 2291/045* (2013.01); *G01N 2291/106* (2013.01); *G01N 2291/2694* (2013.01)

(58) Field of Classification Search
 USPC .................................. 73/597, 599, 600, 602
 See application file for complete search history.

(56) References Cited

U.S. PATENT DOCUMENTS

| | | | | |
|---|---|---|---|---|
| 6,092,420 | A * | 7/2000 | Kimura | G01N 29/043 73/599 |
| 6,397,681 | B1 * | 6/2002 | Mizunoya | G01N 29/0645 73/620 |
| 8,798,940 | B2 * | 8/2014 | Imbert | G01M 13/045 702/35 |
| 2009/0217763 | A1 * | 9/2009 | Yamano | G01N 29/043 73/622 |
| 2010/0126277 | A1 * | 5/2010 | Wu | G01N 29/0654 73/602 |
| 2010/0207620 | A1 * | 8/2010 | Gies | G01N 27/9033 324/240 |
| 2011/0088476 | A1 * | 4/2011 | Yaman | G01N 29/043 73/632 |
| 2011/0113885 | A1 * | 5/2011 | Ueda | G01N 29/069 73/632 |

* cited by examiner

NON-DESTRUCTIVE ULTRASOUND TESTING OF STRUCTURES MADE OF COMPOSITE MATERIAL

This application is a national phase application of International Application No. PCT/EP2013/062518, filed on Jun. 17, 2013, which designated the U.S. and claims priority to France Application No. 1255720, filed on Jun. 19, 2012, the entire contents of each of which are hereby incorporated by reference.

BACKGROUND OF INVENTION

The present invention belongs to the field of non-destructive testing of structures; more particularly, it relates to a device and a method for the ultrasonic non-destructive testing of structures made of laminated composite material, for example panels used to construct the fuselage or wing members of an aircraft.

Panels of laminated composite material are made by stacking a plurality of layers, formed of fibers, which are held together by a hardened resin.

During the life of an aircraft, a panel of laminated composite material used to form the fuselage or wing members is subject to impacts on its free face, called the front face, due, for example, to bird strikes or tools dropped during maintenance operations. These impacts damage the structure of the panel because they give rise to delamination between its layers. Delamination cannot be detected by simple visual inspection alone.

There is a known ultrasonic testing device, described in European patent application EP1759195, for revealing whether delamination is present in the thickness of a panel after an impact. Using a probe in contact with the front face of the inspected panel, this device emits an ultrasonic pulse and receives the pulse reflected by the rear face of the panel, then compares the form and return time of the reflected signal with the form and return time of a signal called the reference signal, which is reflected by the rear face of the panel and is obtained when the panel is intact. A difference in form and return time between the two reflected signals, if beyond acceptable limits, reveals delamination.

Before this device is used, it has to be calibrated on an intact panel having the same dimensions as the panel to be inspected, in order to obtain the form and return time of the reference signal. Because of this calibration, this device is very effective when the panels to be inspected have a constant thickness, but may give erroneous results if the probe is moved over a length of a panel along which the panel exhibits a decreasing thickness, notably a thickness decreasing in steps.

In fact, the fuselage and/or the wing members of some aircraft are formed by panels of laminated composite materials having a non-constant thickness. At the present time, there are no existing effective devices for the ultrasonic non-destructive testing of these panels. The object of the present invention is to overcome this deficiency, at least in part.

SUMMARY OF INVENTION

To this end, the invention proposes a diagnostic apparatus for detecting delamination in the thickness of a laminated composite panel, the apparatus comprising an ultrasonic probe intended to be brought into contact with a face of said panel, said probe comprising a plurality of elementary transducers and an electronic device connected to each of said transducers to control the emission and reception of ultrasonic pulses by said probe by the activation of at least one elementary transducer, the apparatus further comprising a display device having at least a first indicator which can be activated by the electronic device when the latter detects the presence of delamination in the panel, said electronic device being configured to calculate the value of an indicator of the coupling of said probe with said face, and to switch, if the value of the coupling indicator is equal to a predetermined value, from a coupling mode to a scanning mode, the scanning mode being such that, during emission, the electronic device transmits the same pulsed signal successively to the elementary transducers according to a predetermined activation sequence for the elementary transducers, and such that, during reception, the electronic device analyzes the signals received by the elementary transducers so as to detect delamination in a predetermined depth range of the thickness of said panel.

The invention enables a panel to be inspected without any preliminary calibration of the probe on an intact panel having the same dimensions as the panel to be inspected. According to the invention, the check made to ensure correct coupling between the probe and the panel provides assurance that the analyzed depth range in the thickness of the panel is constant, regardless of how thick the panel is. Thus the diagnostic apparatus according to the invention can be used to inspect a panel having decreasing or increasing thickness, notably a thickness decreasing in steps along its length.

SUMMARY OF DRAWINGS

The invention will now be described more precisely in the context of preferred embodiments, which are not limiting in any way, represented in FIGS. 1 to 4, in which.

DETAILED DESCRIPTION OF INVENTION

Figure 1:
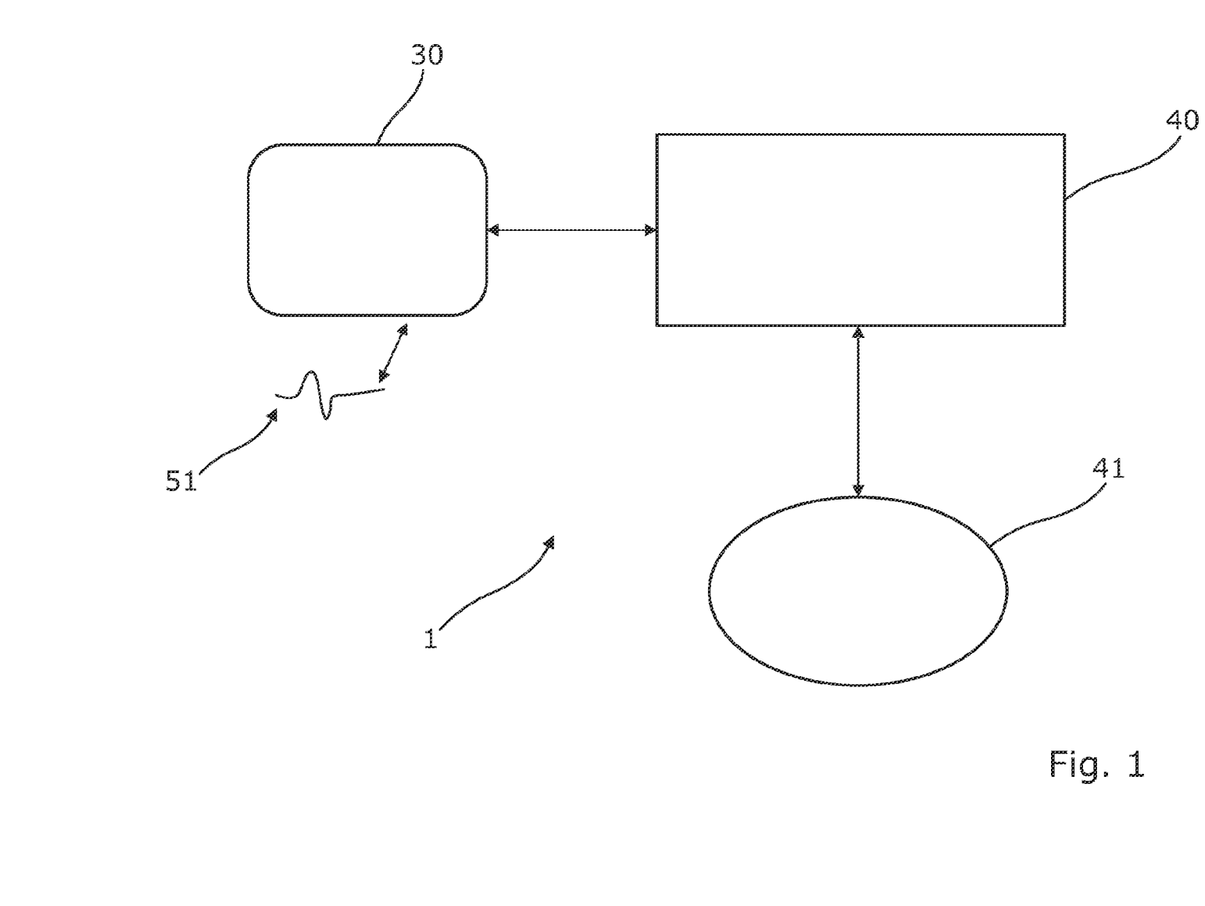
FIG. 1 is a schematic view of a diagnostic apparatus according to one embodiment of the invention, comprising a probe, an electronic device and a display device.

FIG. 1 shows a diagnostic apparatus 1 according to a preferred embodiment of the invention. The diagnostic apparatus 1 is intended to be used for inspecting a panel, for example an aircraft panel, made of laminated composite material, and for detecting any delamination in the thickness of this panel.

The diagnostic apparatus 1 comprises an ultrasonic probe 30, an electronic device 40 for controlling the emission and reception of ultrasonic pulses 51 by the ultrasonic probe 30, and a display device 40 having, notably, indicators showing the presence or absence of delamination in the panel.

The ultrasonic probe 30 is of the roller probe type, comprising, in a known way, a body having a wheel mounted in a freely rotatable manner on one end of the body. The wheel is the element of the probe which is intended to be brought into contact with the front face of the panel to be inspected. In order to carry out the inspection of a panel, a plurality of elementary transducers forming a network of elementary transducers is fixed to the hub of the wheel.

Figure 2:
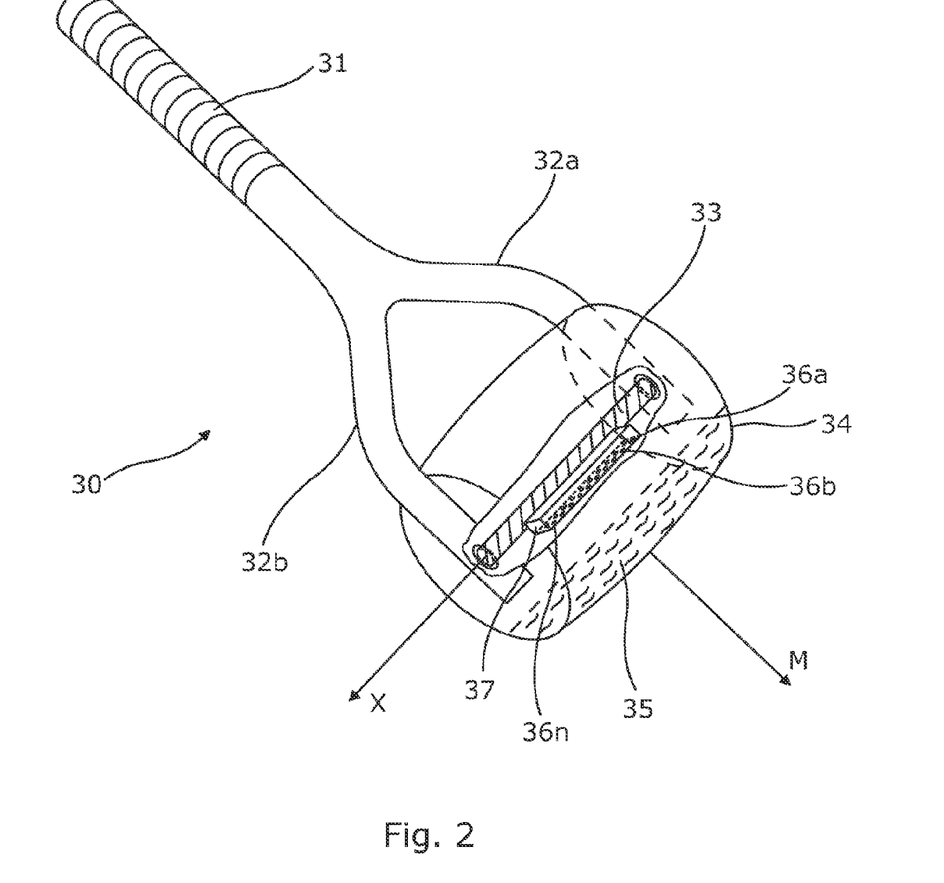
FIG. 2 is a schematic view of the probe of FIG. 1.

According to the example shown in FIG. 2, the body of the probe 30 is fork-shaped, comprising a cylindrical tube 31 extended by two branches 32a, 32b. The free end of the cylindrical tube forms a handle for an operator. A free-running wheel 34 is fitted in the space formed by the two branches 32a, 32b by means of a hub 33. The hub 33 is fixed with respect to the two branches 32a, 32b.

The wheel 34 takes the form of a tire made with a substantially cylindrical rubber membrane. The membrane encloses a liquid 35, which is neutral to ultrasonic waves, and the network of elementary transducers 36a, 36b, . . . , 36n, which is arranged on a support 37 of the parallelepipedal type, fixed to the hub 33 as shown in FIG. 2. The support 37 is fixed by a first face to the hub of the wheel, and the elementary transducers 36a, 36b, . . . , 36n are all positioned on the face of the support 37 which is opposed to the first face, in such a way that all the elementary transducers 36a, 36b, . . . , 36n emit ultrasonic pulses in the same direction, called the inspection direction M. In the illustrated example, the inspection direction M is substantially aligned with the longitudinal axis of the tube 31.

When the diagnostic apparatus 1 according to the invention is in use, the wheel 34 of the probe 30 is applied, in the position of use, to the front face of a panel to be inspected, so that the inspection direction M is substantially parallel to the transverse direction of the panel. The probe 30 is advantageously adapted to be moved, by means of its wheel 34, over the front face of the panel. When the wheel 34 moves, the network of elementary transducers 36a, 36b, . . . , 36n is immersed in the liquid 35 so that the latter forms a interface neutral to ultrasonic waves between the network of elementary transducers 36a, 36b, . . . , 36n and the rubber membrane of the wheel 34.

Each elementary transducer 36a, 36b, . . . , 36n is a piezoelectric transducer which can be activated for both emission and reception to emit and receive, respectively, ultrasonic pulses. In the remainder of the description, an ultrasonic pulse emitted by an elementary transducer 36a, 36b, . . . , 36n after its activation for emission will be called a "burst".

Figure 3:
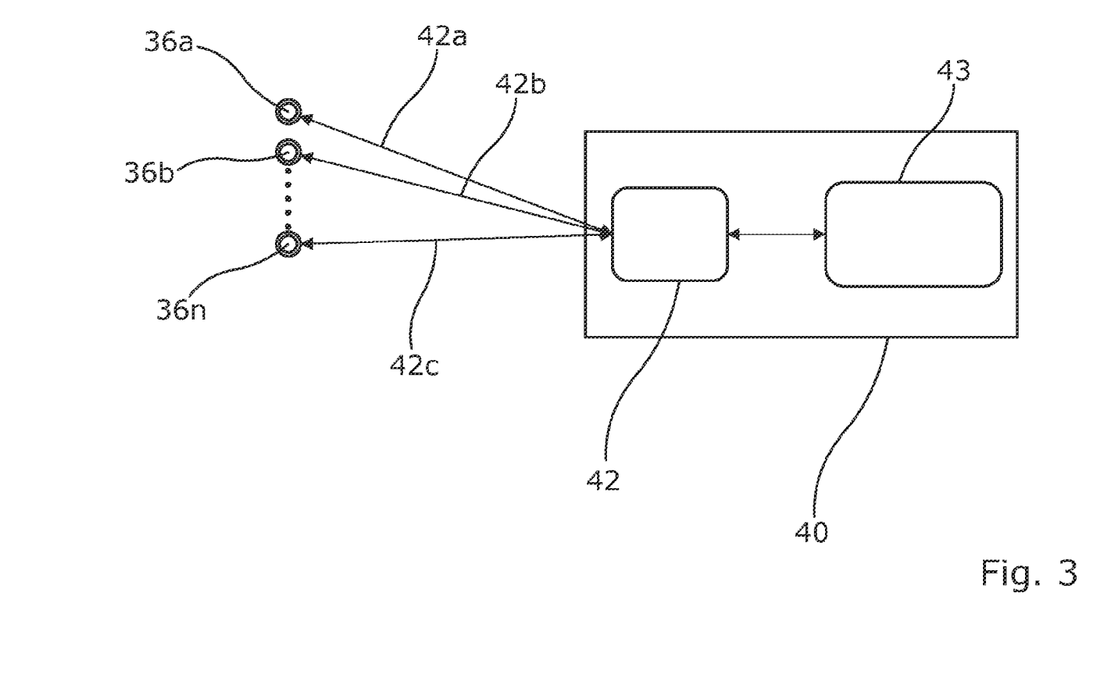
FIG. 3 is a representation of the electrical connections between the various elements making up the diagnostic apparatus of the invention.

FIGS. 1 and 3 show an electronic device 40 which controls the activation of the elementary transducers 36a, 36b, . . . , 36n of the network for transmission and reception. The electronic device 40 comprises an ultrasonic acquisition card 42 and a central unit 43.

The ultrasonic acquisition card 42 comprises a programmable logic circuit and elements such as analog-digital converters for transmitting digital signals to the central unit 43, amplifiers, and filters. The ultrasonic acquisition card 42 is housed in the tube 31 of the probe 30. The ultrasonic card 42 is connected to each elementary transducer 36a, 36b, . . . , 36n of the network via a wire link 42a, 42b, . . . , 42n. Any one of the elementary transducers 36a, 36b, . . . , 36n can therefore be activated, by the acquisition card 42, independently of the others. A pulse signal sent by the ultrasonic acquisition card 42 to an elementary transducer 36a, 36b, . . . , 36n via the corresponding wire link 42a, 42b, . . . , 42n between the elementary transducer 36a, 36b, . . . , 36n and the acquisition card 42 is converted to an ultrasonic pulse 51 by the transducer. Conversely, when an elementary transducer 36a, 36b, . . . , 36n receives an ultrasonic pulse 51, it sends a pulse signal corresponding to the received ultrasonic pulse to the acquisition card 42, via the corresponding wire link 42a, 42b, . . . , 42n between the elementary transducer 36a, 36b, . . . , 36n and the acquisition card 42.

The acquisition card 42 is also connected by a USB wire link or a wireless link of the Wi-Fi type to the central unit 43. The central unit 43 comprises, in a known way, at least one processor, memories, and peripheral units and input-output interfaces. The central unit 43 executes a program for controlling the emission and reception of ultrasonic pulses by the network of ultrasonic transducers 36a, 36b, . . . , 36n via the acquisition card 42, and also for processing and analyzing the signals corresponding to the ultrasonic pulses 51 received by the acquisition card 42.

Advantageously, the electronic device 40 can be switched to two different modes, namely the coupling mode and the scanning mode. In coupling mode, the central unit 43 determines whether the probe 30 is correctly coupled to the front face of the panel to be analyzed, whereas in scanning mode the central unit 43 determines whether an inspected panel does or does not exhibit delamination. The check of the correctness of the coupling between the probe 30 and the front face of the panel is performed by the central unit 43 which determines, in coupling mode, whether a Boolean coupling indicator has a value of 1, as described below.

In both modes, the form of the pulse signal sent to one elementary transducer 36a, 36b, . . . , 36n is the same for the other elementary transducers.

In the coupling mode, the elementary transducers 36a, 36b, . . . , 36n are all activated for emission or reception at the same time, and each signal supplied by an elementary transducer to the electronic device 40 is amplified so that the signals supplied by the elementary transducers 36a, 36b, . . . , 36n all have the same amplitude.

In this mode, as described below, the central unit 43 causes the display of at least one luminous indicator present on the display device 41 following the results of the analysis of the signals supplied by the elementary transducers 36a, 36b, . . . , 36n to the electronic device 40.

In the scanning mode, the elementary transducers 36a, 36b, . . . , 36n are activated successively according to an activation sequence, in both emission and reception.

In emission, the multiple bursts, which have phase lags (delays) between them, can be used to create a beam by constructive interference. This is because the multiple bursts are added to a single wave front moving at an angle, called the scanning angle, defined with respect to the inspection direction M. By modifying the phase lags from one burst to the next, the scanning angle is modified. The signal supplied by the central unit 43 to the acquisition card 42 then comprises, in addition to the form of the pulse signal to be converted to an ultrasonic pulse by the elementary transducers 36a, 36b, . . . , 36n, the activation sequence and the phase lag between the bursts. The phase lag between the bursts is advantageously determined as a function of the speed of movement of the wheel 34 over the front face of the panel, determined by means of the sensors arranged on the probe 30.

In reception, a multitude of ultrasonic pulses with phase lags between them is received by the network of elementary transducers 36a, 36b, . . . , 36n. For each activation sequence, the acquisition card 42 reconstitutes a signal, called the scanning signal, on the basis of the characteristics (amplitude, form and phase) of the various pulses received, the time of flight of each of the pulses received, and the scanning angle. Thus the scanning signal comprises amplitude and time data corresponding to amplitudes and arrival times of the pulses received.

In use, as described below, that is to say during the inspection of a panel, the scanning signal represents the ultrasonic echo profile returned by the panel.

The expression "time of flight" of a received pulse means the time elapsed between the moment of emission of an ultrasonic pulse by an elementary transducer 36a, 36b, . . . , 36n and the moment of reception, by the same elementary transducer, of the same ultrasonic pulse reflected by a discontinuity in the medium.

The acquisition card 42 then digitizes the scanning signal and transmits it to the central unit 43, which processes and analyzes the scanning signal, as described below.

Following the results of the analysis of the scanning signal, the central unit 43 causes the indicators to be displayed on the display device 41, for reading by an operator using the diagnostic apparatus of the invention.

Figure 4:
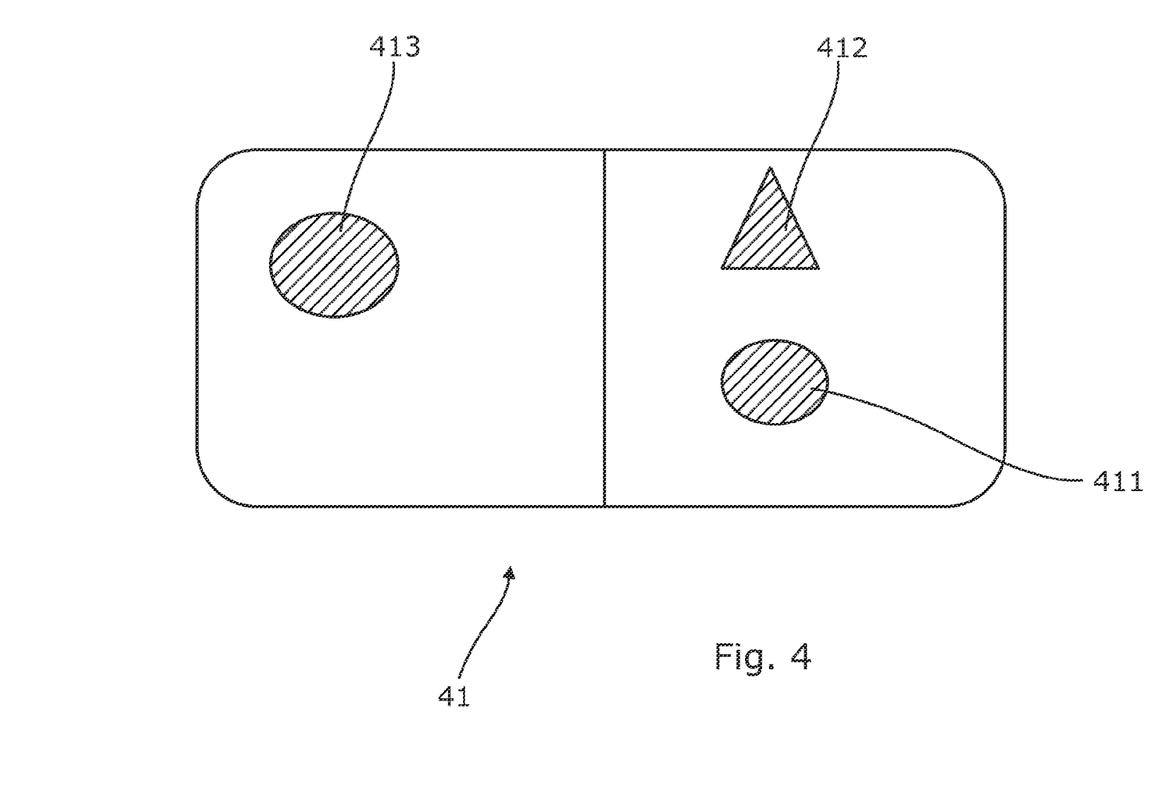
FIG. 4 is a view of the face of the display device of FIG. 1 which comprises, notably, a plurality of luminous indicators.

The display device 41, shown in FIG. 4, includes:
- a first luminous indicator 411 which, when activated, indicates that no delamination has been detected within the inspected panel;
- a second luminous indicator 412 which, when activated, indicates that delamination has been detected within the inspected panel; and
- a third luminous indicator 413 which, when activated, indicates that the coupling between the ultrasonic device and the front face 11 of the area of the panel to be inspected is correct.

The method for detecting delamination in a panel, shown in FIG. 5, using the detection apparatus according to the invention, will now be described.

In a first step, the electronic device 40 operates in coupling mode to check that a Boolean coupling indicator, indicative of the coupling between the panel 10 to be inspected and the probe 30, has the value of 1.

In this first step, and if the probe 30 is in a vacuum, the central unit 43 measures, for each elementary transducer 36a, 36b, . . . , 36n, the time of flight, called the time of flight in vacuo, of the first pulse received. The first pulse received corresponds to an ultrasonic pulse reflected by the membrane of the wheel 34 when the latter is not in contact with the panel to be inspected. The central unit 43 also analyzes the form, called the reference form, of the signal corresponding to the first pulse received.

Figure 5:
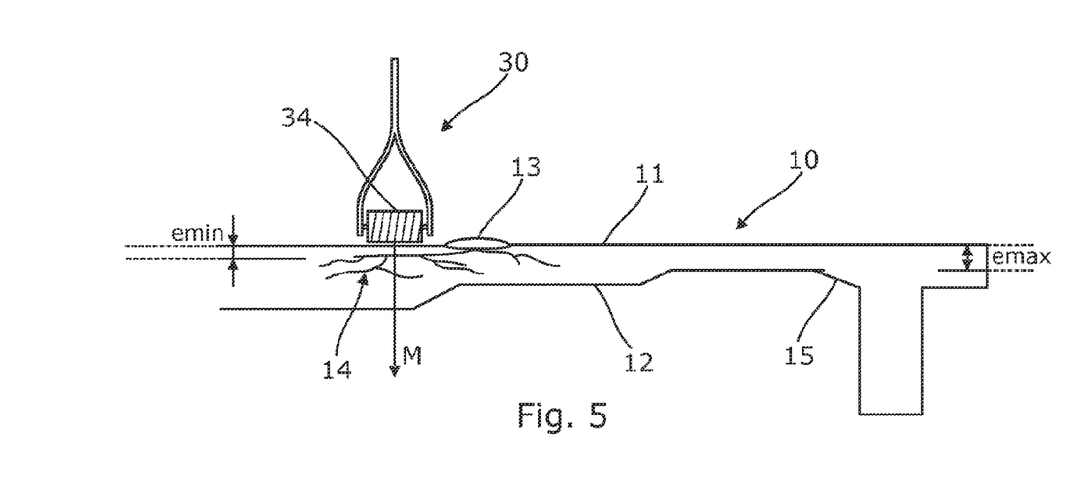
FIG. 5 is a cross-sectional view of the thickness of a panel inspected by the diagnostic apparatus according to the invention, the panel having been subjected to an impact on its front face which has given rise to delamination.

When the probe is in the position of use, as shown in FIG. 5, the central unit 43 measures, for each burst, the time of flight, called the coupling time of flight, of the first pulse received. This time, the first pulse received corresponds to an ultrasonic pulse reflected by the membrane of the tire of the wheel 34 when the latter is in contact with the front face 11 of the panel 10 to be inspected. The central unit 43 then subtracts the value of the coupling time of flight from the value of the time of flight in vacuo. If the result of the subtraction is below an adjustable threshold, a first Boolean indicator of the coupling of the elementary transducer is set to the value of one (in positive logic).

Finally, a first global indicator of coupling is set to the value of one if the number of first indicators set to one is above an adjustable threshold.

The first global indicator of coupling set to the value of one indicates that the probe 30 is being used correctly, and therefore that the wheel 34 is correctly deformed as a result of being applied to the front face 11 of the panel 10.

Subsequently, and for each elementary transducer 36a, 36b, . . . , 36n, the central unit 43 measures the rate of deformation of the form of the pulse signal reflected by the front face 11 of the panel 10 after a burst with the form of the reference signal. The deformation is due to the difference in impedance between the media (rubber/composite material) through which the pulse passes. If the reference signal is of the Gaussian pulse type, the central unit 43 uses, for example, two digital acquisition ports to detect the position of the positive and negative alternations of the pulse signal reflected by the front face of the panel relative to those of the Gaussian pulse.

If the rate of deformation is above a predetermined rate of deformation, threshold, a second Boolean indicator of the coupling of the elementary transducer is set to one, in positive logic.

Finally, a second global indicator of coupling is set to one if the number of second indicators set to one is above an adjustable threshold. The second global indicator of coupling set to one indicates that a pure layer of coupling agent is present between the membrane of the wheel 34 and the panel 10.

The central unit 43 then executes a logical AND operation between the first global coupling indicator and the second global coupling indicator. The Boolean result of the logical AND operation is called the coupling indicator. In the coupling mode, the central unit 43 continuously compares the value of the coupling indicator with the value 1. If the coupling indicator has a value of 1, the central unit 43 determines that the probe 30 is coupled to the front face 11 and causes the indicator device 41 to activate the third indicator 413.

When the probe 30 has been coupled, that is to say when the coupling indicator has a value of 1, the electronic device 30, in a second step, automatically switches to scanning mode, and the scanning of the panel 10 starts for a first activation sequence. As described above, the acquisition card 42 reconstitutes the scanning signal 33b, represented in FIG. 6, on the basis of the received pulses. The scanning signal 33b represents the ultrasonic echo profile of the panel 10.

The ultrasonic pulses emitted by the elementary transducers 36a, 36b, . . . , 36n during an activation sequence pass through the thickness of the panel 10 and are reflected from elements such as the surfaces of the panel 10, the corners 15, and other discontinuities such as delaminations 14.

Figure 6:
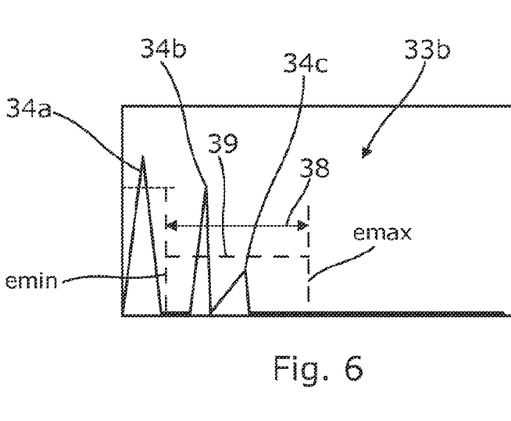
FIG. 6 is the echo profile, produced by the electronic device, of the inspected panel shown in FIG. 5.

These reflections are manifested by peaks 34a, 34b, 34c in the scanning signal 33b. Thus the scanning signal 33b typically comprises a plurality of peaks 34a, 34b, 34c offset in time, each peak corresponding to at least one pulse reflected by an element of the panel 10. The horizontal time axis t of the scanning signal 33b shows the times of flight of the received pulses. Therefore, the time shift between the peaks 34a, 34b, 34c is a function of the time of flight of the received pulses, which have been reflected by the elements 11, 14, 15 of the panel.

On the basis of the speed of ultrasonic waves, this time shift can therefore be used to determine the distance between the elements 11, 14, 15 of the panel 10 and the depth of the elements in the thickness of the panel 10. A peak 34a, 34b, 34c corresponding to an element 11, 14, 15 of the panel 10 has an amplitude which increases with a rise in the number of pulses reflected by this element 11, 14, 15 in an activation sequence.

In order to detect the presence of delamination, the central unit 43 determines whether peaks 34b, 34c present in the scanning signal have an amplitude above a predetermined threshold 39 and lie within a predefined time window 38. The predetermined amplitude threshold makes it possible to consider only the peaks 34b, 34c which reveal the presence of delamination, rather than parasitic noise.

In FIG. 6, the diagnostic apparatus 20 is inspecting the panel shown in FIG. 5, which has been subjected to an impact 13 on its front face 11 which has given rise to delamination 14. The ultrasonic device 30 is shown as being applied to the front face 11 of the panel, in the immediate proximity of the impact 13.

The time window 38 represents a depth range in the thickness of the panel, varying between a minimum thickness $e_{min}$ and a maximum thickness $e_{max}$, starting from the front face 11 of the panel and measured along the transverse direction of the panel. The depth $e_{min}$ corresponds to a thickness that is strictly greater than that of a time of flight of a received pulse corresponding to the pulse 34a reflected by the front face 11, which would not be representative of delamination 14. The depth $e_{max}$ corresponds to a depth that is strictly less than that of a time of flight of a received pulse which would be reflected by an element located at a distance $e_{max}$ from the front face.

Typically, the depth $e_{max}$ is chosen so as to be less than half of the known thickness of the panels 10 of laminated composite used to form the structure of the aircraft.

For the current activation sequence of the network of elementary transducers 36a, 36b, . . . , 36n, a peak 34b having an amplitude greater than the amplitude threshold 39 is present in the time window 38. The peak 34 therefore signifies a delamination 14 present in the thickness of the panel 10. The central unit 43 then causes the display device 41 to activate the second indicator 412.

If no peak with an amplitude above the amplitude threshold 39 had been detected in the time window 38, the central unit 43 would have caused the display device to activate the first indicator 411.

It should be noted that, during the use of the diagnostic apparatus 1, the electronic device switches into coupling mode at regular intervals of time, in order to check the correctness of the coupling between the probe 30 and the panel 10 to be inspected. If the coupling is correct, the electronic device automatically switches to scanning mode as described above.

It will be understood from the above description that the diagnostic apparatus 1 according to the invention for detecting delamination 14 in the thickness of a panel 10 of laminated composite can be used to inspect a panel 10 having a non-constant thickness along its length.

The signal reflected by the rear face 12 of a panel 10 inspected by the diagnostic apparatus 1 according to the invention, when the probe 30 of the apparatus is placed on the front face 11 of the panel, is therefore not used for making the decision as to the presence or absence of delamination. In fact, an analysis of the scanning signal over a restricted depth range of the panel 10 is sufficient, because delamination caused by an impact 13 on the front face 11 of a panel of laminated composite material typically commences at the first interfaces of the layers of the stack, at the front face of the panel, and propagates into the interfaces of subsequent layers, according to a conical expansion model, toward the rear face 12 of the panel.

In order to use the diagnostic apparatus according to the invention, it is simply necessary to check the correctness of the coupling between the probe 30 and the panel 10 to be inspected, thereby ensuring, notably, that the analyzed depth range (in the time window 38) is constant regardless of how thick the panel is. Thus, unlike prior art devices, the diagnostic apparatus 1 according to the invention does not have to be calibrated for constant panel thicknesses.

It should also be noted that the diagnostic apparatus 1 of the invention operates in a simple way and provides an intuitive readout of the results. Thus it can easily be used by an operator without a high level of qualification in non-destructive testing methods. Thus any person on the ground at an airport, if provided with this diagnostic apparatus, can rapidly learn how to operate it and use it to determine whether or not a visible impact on an inspected aircraft structure has caused structural damage such as delamination, and whether specialist inspection staff should be called in. The immobilization of the aircraft on the ground is only recommended if necessary.

Although the display device has been described as having luminous indicators, the indicators are audible in a variant of the display device. In another variant of the display device, the indicators are both audible and luminous.

The invention claimed is:

1. A diagnostic apparatus for detecting delamination in the thickness of a laminated composite panel, which apparatus comprises:
   an ultrasonic probe configured to be brought into contact with a face of said panel and moved over said face, said probe comprising a wheel housing a plurality of elementary transducers, wherein the wheel is configured to be placed into contact with the laminated composite panel, and
   an electronic device connected to each of said transducers to control emission and reception of ultrasonic pulses by said probe by the activation of at least one of the elementary transducers,
   a display device having at least a first indicator configured to be activated by the electronic device when the electronic device detects a presence of delamination in the panel,
   said electronic device configured to calculate a value of a coupling indicator of a coupling of said ultrasonic probe with said face, and to switch, if the value of the coupling indicator is equal to a predetermined value, from a coupling mode to a scanning mode, the scanning mode being such that, during emission, the electronic device transmits a pulsed signal successively to the elementary transducers according to a predetermined activation sequence for the elementary transducers, and such that, during reception, the electronic device analyzes reflections of the pulsed signals received by the elementary transducers to detect delamination in a predetermined depth range of a thickness of said panel,
   wherein the predetermined depth range is defined by a minimal depth and a maximum depth, and the minimal depth is a depth below a surface of the laminated composite panel in contact with the wheel and the maximum depth is a depth less than a thickness of the laminated composite panel.

2. The diagnostic apparatus as in claim 1, wherein, in the coupling mode, during transmission, the electronic device transmits the same pulse signal simultaneously to each of the elementary transducers, and, during reception, the electronic device analyzes the signals received by the elementary transducers to calculate the value of the coupling indicator.

3. The diagnostic apparatus as in claim 1, wherein the display device further comprises a second indicator configured to be activated by the electronic device when this device is switched to scanning mode.

4. A method for detecting delamination in a panel of laminated composite, said panel having a front face, said method using a diagnostic apparatus including: an ultrasonic probe comprising elementary transducers, an electronic device connected to each of the elementary transducers, and a display device having at least a first indicator,
wherein the method includes the following successive steps:
a) while the ultrasonic probe is in contact with the front face, emitting ultrasonic pulses from the elementary transducers into the panel and receiving ultrasonic pulses reflected by the panel;
b) calculating a value of a coupling indicator representing a coupling of the probe with the front face, wherein the calculation is performed using data representing the emitted ultrasonic pulses and the received ultrasonic pulses;
c) comparing a value of the coupling indicator with a predetermined value;
d) for activating sequence of the elementary transducers, and if the value of the coupling indicator is equal to said predetermined value:
1) emitting an ultrasonic pulse by each of the plurality of elementary transducers toward the panel;
2) receiving by each of the elementary transducers a pulse reflected by the panel;
3) reconstituting, by the electronic device of a scanning signal, based on the plurality of reflected pulses received;
e) activating an indicator of the means of presenting the information indicative of the presence of delamination in the thickness of said panel when the scanning signal has a peak having an amplitude above a predefined threshold, representing a time of flight of a received pulse whose duration is:
greater than that of a time of flight of a received pulse corresponding to the pulse reflected by said front face, and
less than that of a time of flight of a received pulse which would correspond to the pulse reflected by an element located at a distance emax from said front face.

5. The method as claimed in claim 4, wherein the value of the coupling indicator is equal to the predetermined value when:
A) a result of a subtraction between a time of flight of a pulse received by one of the elementary transducers when the probe is in contact with the front face of the panel and a time of flight of a pulse received by the one of the elementary transducers when the probe is not in contact with said front face is shorter a predetermined threshold,
B) a rate of deformation of a pulse reflected by said front face and received by the one of the elementary transducers when the probe is in contact with said front face is greater than a predetermined rate of deformation; and
C) the results of steps A and B are valid for a number of the elementary transducers greater than a predetermined number.

6. The method as claimed in claim 4, wherein the distance emax is less than half of a known thickness of the panel.

7. The method as claimed in claim 4, wherein the steps of the calculation of the value of the coupling indicator and comparing the value to the predetermined value are performed at regular time intervals.

8. A method to detect delamination in a panel of a laminated composite layers using an ultrasonic probe, the method comprising:
while the ultrasonic probe is in contact with a surface of the panel, repeatedly emitting ultrasonic signals from the probe into the panel and receiving ultrasonic reflections of the emitted signals by the probe, wherein a time of flight is a period between emitting one of the ultrasonic signals and receiving a reflection of the one of the ultrasonic signals;
analyzing the received ultrasonic reflections to determine a minimum time of flight as corresponding to the ultrasonic signals reflected by the surface of the panel;
establishing as a minimum period greater than the minimum time of flight;
establishing a time of flight range bounded by the minimum period and a maximum period, wherein maximum period corresponds to a period for the ultrasonic signals to be reflected at a certain depth in the panel and the certain depth is shallower than a thickness of the panel;
as the ultrasonic probe moves over the surface of the panel, analyzing the received ultrasonic reflections to determine whether the received reflections received within the established time of flight range exceed a threshold level, and
issuing an indication of a delamination in the panel in response to the determination that the received reflections exceed the threshold level.

9. A diagnostic apparatus comprising:
an ultrasonic probe including a deformable wheel configured to be brought into contact with a surface of a laminated composite component, elementary transducers within a cavity of the wheel and a liquid within the cavity which is neutral to ultrasonic waves from the elementary transducers;
an electronic device controlling each of the elementary transducers and configured to control emission and reception of ultrasonic pulses by the activation of one or more of the elementary transducers,
a display device presenting at least a first indicator in response to a signal from the electronic device made in response to the electronic device detecting a delamination in the laminated composite component,
the electronic device is configured to calculate a value of a coupling indicator of a coupling of said ultrasonic probe with said face, and to switch, if the value of the coupling indicator corresponds to a predetermined value, from a coupling mode to a scanning mode, and the electronic device analyzes reflections of ultrasonic signals received by the elementary transducers to detect a delamination in a predetermined depth range of a thickness of said laminated composite component.

* * * * *